ent ct Patent

United States Patent [19]
Mutai et al.

[11] 4,347,240
[45] Aug. 31, 1982

[54] **ANTITUMOR AGENT CONTAINING *LACTOBACILLUS CASEI* YIT 9018**

[75] Inventors: Masahiko Mutai, Higashi Yamato; Teruo Yokokura, Tokyo; Seizaburo Kobayashi; Ikuo Kato, both of Hachioji, all of Japan

[73] Assignee: Kabushiki Kaisha Yakult Honsha, Tokyo, Japan

[21] Appl. No.: 124,725

[22] Filed: Feb. 26, 1980

[30] Foreign Application Priority Data

Feb. 27, 1979 [JP] Japan .................................. 54-21339

[51] Int. Cl.$^3$ .............................................. A61K 39/02
[52] U.S. Cl. ......................................... 424/92; 424/93
[58] Field of Search .................................... 424/92, 93

[56] References Cited

FOREIGN PATENT DOCUMENTS 43-6690  3/1968  Japan .
45-28558  9/1970  Japan .

*Primary Examiner*—Shep K. Rose
*Attorney, Agent, or Firm*—Wenderoth, Lind & Ponack

[57] ABSTRACT

Immunostimulating agent for inhibiting tumors comprising *Lactobacillus casei* YIT 9018 and methods for treating and/or preventing tumor growth.

8 Claims, No Drawings

ANTITUMOR AGENT CONTAINING *LACTOBACILLUS CASEI* YIT 9018

BACKGROUND OF THE INVENTION

This invention relates to an antitumor agent containing *Lactobacillus casei* YIT 9018 (Deposit No. FERM-P 4751) as an effective ingredient. This strain is deposited at Fermentation Research Institute, Government Industrial Research, Ministry of International Trade and Industry, Japan.

While the antitumor activity of a live streptococcal preparation (Japan Tokkyo Koho, 6690, 1968) or an extract from lactobacilli (Japan Tokkyo Koho, 28558, 1970) has been reported, it has not been known that the heat-killed whole cell preparation has an antitumor activity.

SUMMARY OF THE INVENTION

This invention is concerned with the antitumor activity of not only live but also heat-killed *Lactobacillus casei* YIT 9018 whole cells. This provides the following benefits: the process of preparation is simpler, and the side effects of the additives for maintaining the survival of the bacteria can be prevented. It also deserves a special emphasis that *Lactobacillus casei* YIT 9018 is non-toxic and is practically used in a fermented milk product.

DETAILED DESCRIPTION OF THE INVENTION AND ITS PREFERRED EMBODIMENTS

It has been shown that *Lactobacillus casei* YIT 9018 (Deposit No. FERM-P 4751) (hereinafter referred to as "LC 9018") has a higher antitumor activity compared to other lactobacilli. This bacterial strain exhibited antitumor activity against solid and ascites tumor of Sarcoma 180 with intravenous, subcutaneous, oral or intraperitoneal administration in mice. Furthermore, it showed an antitumor activity against mouse leukemia L1210 or P-388 on which commercial antitumor streptococcal preparation had no effect. In addition, the toxicity of LC 9018 was significantly lower than those of other lactobacilli and streptococcal antitumor agents.

LC 9018 was cultivated on a broth containing (per 1000 ml of distilled water)

Trypticase—10 g
Yeast extract—5 g
Tryptose—3 g
$K_2HPO_4$—3 g
$KH_2PO_4$—3 g
Ammonium citrate—2 g
Sodium acetate—1 g
Tween 80 —80 g
Glucose—20 g
Cystein—0.2 g
$MgSO_4\text{-}7H_2O$—0.5 g
$FeSO_4\text{-}7H_2O$—0.04 g
$MnSO_4\text{-}2H_2O$—0.12 g at 37° C. for 20-40 hr. After cultivation, the cells were washed with distilled water and lyophilized.

EXPERIMENT 1: ANTITUMOR ACTIVITY OF LC 9018

EXAMPLE (1)

Sarcoma 180 ($1-2\times 10^6$ cells/mouse) was implanted into ICR male mice subcutaneously on day 0. A suspension of lactobacilli in saline (0.25 mg/mouse) was injected intravenously daily on days $+1-+5$. Mice were dissected 3 weeks after the tumor implantation and the weight of the tumor was measured. The inhibition rate was calculated according to the formula:

$$\text{Inhibition rate} = \left(1 - \frac{\text{Average tumor weight of tested mice}}{\text{Average tumor weight of control mice}}\right) \times 100.$$

As shown in Table 1, other lactobacilli had inhibition rates of 40–70% as did the streptococcal preparation. LC 9018 showed an inhibition rate of more than 80%.

EXAMPLE (2)

Sarcoma 180 ($1-2\times 10^6$ cells/mouse) was implanted subcutaneously into male ICR mice after being admixed with 1 mg of LC 9018. The inhibition rate with LC 9018 was 97.3%, determined as described in Example (1).

EXAMPLE (3)

Sarcoma 180 ($1-2\times 10^6$ cells/mouse) was inoculated subcutaneously followed by the subcutaneous injection of LC 9018 24 hr after the tumor implantation. As shown in Table 2, LC 9018 significantly inhibited the growth of Sarcoma 180 at the dose of 40 mg/kg.

EXAMPLE (4)

Sarcoma 180 ($1-2\times 10^6$ cells/mouse) was inoculated subcutaneously into male ICR mice on day 0. LC 9018 was given orally daily on days $-10$, $+1$, and $+10$. It was found LC 9018 showed antitumor activity even by oral administration (Table 3).

EXAMPLE (5)

Sarcoma 180 ($1-2\times 10^6$ cells/mouse) was inoculated intraperitoneally on day 0. LC 9018, suspended in saline, was injected intraperitoneally daily on days $-5--1$. The relative survival rate (T/C %) was calculated as follows:

$$T/C \% = \frac{\text{Average survival time of tested mice}}{\text{Average survival time of control mice}} \times 100.$$

As shown in Table 4, LC 9018 increased the survival time of mice with implanted tumor cells.

EXAMPLE (6)

Mouse leukemia L1210 or P-388 ($1\times 10^5$ cells/mouse) was inoculated intraperitoneally into male $BDF_1$ mice on day 0. LC 9018, suspended in saline, was given intraperitoneally daily on days $+1-+5$. As shown in Table 5, LC 9018 also inhibited the growth of leukemia cells. This should be emphasized because the commercial streptococcal preparation has no antitumor activity against leukemia.

EXPERIMENT 2: TOXICITY OF LC 9018

(1) $LD_{50}$

The $LD_{50}$ of lactobacilli which showed an inhibition rate (Table 1) of more than 40% was determined using ICR mice according to the method of Litchifield-Wilcoxon. LC 9018 was less toxic compared to streptococcal preparation as well as other lactobacilli (Table 6).

(2) Antigenicity

LC 9018 was injected subcutaneously into white guinea pigs three times every 3 days at the total dose of 50 mg/kg. The anaphylactic reaction test and agglutination test were carried out 10 days and 12 days after the final injection of LC 9018, respectively. All the guinea pigs given LC 9018 showed negative reactions in both tests.

EXPERIMENT 3: ANTITUMOR ACTIVITY AND TOXICITY OF HEAT-KILLED LC 9018

The antitumor activity and the toxicity of heat-killed LC 9018 were the same as those of live cells.

LC 9018 has the following characteristics:
Cell shape—short rod
Gram's stain—positive
Optimal pH for growth—6.6–7.0 (at 35°–39° C.)
Range of temperature for growth—15°–42° C.
Methyl red test—negative
Voges-Proskauer reaction—negative
Production of indole—negative
Production of $H_2S$—negative
Ammonia from arginine—negative
Reduction of nitrate—negative
Production of catalase—negative
Liquefaction of gelatin and casein—negative
Citrate utilization—negative
Coagulation of milk—positive
Reduction of litmus milk—positive
Utilization of ammonium and urea—negative
Gas frpm glucose—negative
Fermentation
   arabinose—negative
   xylose—negative
   rhamnose—negative
   glucose—positive
   mannose—positive
   galactose—positive
   sucrose—positive
   maltose—positive
   lactose—positive
   cellobiose—positive
   trehalose—positive
   melibiose—negative
   raffinose—negative
   melezitose—positive
   mannitol—positive
   sorbitol—positive
   salicin—positive
   amygdalin—positive LC 9018 can be cultured according to an ordinary method. For example, it can be cultivated on a semisynthetic broth containing lactose, glucose peptone, yeast extract, $KH_2PO_4$, $K_2HPO_4$, $MgSO_4$ etc. The cultivation was performed at 37° C. for 18–24 hr. After cultivation, bacterial cells were collected by centrifugation and washed with distilled water and lyophilized. While the bacterial cells required no additives for maintaining their survival, it is possible to add certain drugs or substances for maintaining quality as needed.

LC 9018 was suspended in physiological saline for use as an injection. The daily effective doses were 30–100 mg/kg (ideally 50 mg/kg) for intravenous injection, 5–20 mg/kg (ideally 10 mg/kg) for intraperitoneal injection and 1000–2000 mg/kg for oral administration. The frequency and duration of the administration should be varied according to the condition of the patient.

As mentioned above, not only live but also heat-killed LC 9018 had a significant antitumor activity, and it was not pathogenic. Also, the process for preparing, and the clinical usages of, LC 9018 preparations, are not limited, and could be accomplished economically.

EXAMPLE OF PREPARATION (1) LC 9018 ($1 \times 10^7$ cells) was inoculated into 1000 ml of the broth mentioned above and was cultivated at 37° C. for 20 hr. The final live cell number reached at maximum ($2.5 \times 10^9$/ml). The cells were collected by centrifugation and washed with distilled water. The suspension of LC 9018 in distilled water was divided in ampoules and lyophilized. After storing at 5° C. for 30 days, LC 9018 in ampoules was used for the antitumor experiment. The inhibition rate was 83.2%.

(2) LC 9018 was obtained as in (1). It was autoclaved at 121° C. for 20 min and dried at 80° C. The powder was divided into ampoules and stored at 5° C. for 2 months. The inhibition rate against Sarcoma 180 with this preparation was 78.5% and the $LD_{50}$ was 620 mg/kg or 720 mg/kg in male or female ICR mice, respectively.

(3) The culture broth, 300 ml, containing $2.5 \times 10^9$ cells/ml of LC 9018 was inoculated into 10 liters of Rogosa's medium. The cell number was $2.3 \times 10^9$/ml after the cultivation at 37° C. for 20 hr. The wet cells (165 g) were dried at 80° C. for 3 hr and 40 g of powder was obtained. The powder was added to 40 ml of hydroxypropyl cellulose solution (10%) in ethanol and granulated followed by drying. The granules were given orally at the dose of 0.3 g/kg/day for 10 days to ICR mice which had been implanted subcutaneously with Sarcoma 180 ($1-2 \times 10^6$ cells/mouse) 10 days before the oral administration of the granules. The inhibition rate at 3 weeks after the tumor implantation was 68.2%.

TABLE 1

| Antitumor activity of lactobacilli | |
|---|---|
| Strain or preparation | Inhibition rate* |
| L. casei YIT 9018 (LC 9018) | 82.7 |
| L. casei N VIII - 1 | 65.5 |
| L. casei TK IV - 2 | 66.6 |
| L. acidophilus B-3208 | 23.0 |
| L. acidophilus YIT 0163 | 43.5 |
| L. salivarius YIT 0089 | 21.5 |
| L. salivarius YIT 0104 | 40.9 |
| L. fermentum YIT 0082 | 14.9 |
| L. fermentum YIT 0159 | 10.2 |
| L. plantarum YIT 0102 | 17.2 |
| L. plantarum YIT 0158 | 40.4 |
| L. bulgaricus YIT 0046 | 64.7 |
| L. jugurti YIT 0085 | 17.7 |
| L. helveticus YIT 0083 | 29.0 |
| L. lactis YIT 0086 | 12.8 |
| L. leichmannii YIT 0087 | 28.4 |
| L. delbrueckii YIT 0080 | 47.9 |
| L. brevis YIT 0076 | 5.3 |
| L. jensenii YIT 0084 | 38.4 |
| Streptococcal preparation | 50.8 |

Sarcoma 180 ($1-2 \times 10^6$ cells/mouse) was implanted into ICR mice subcutaneously on day 0. The suspension of lactobacilli or streptococcal preparation in saline (0.25 mg/mouse) was injected intravenously daily on days $+1-+5$.

*Inhibition rate $= \left( \dfrac{\text{Average tumor weight of tested mice}}{\text{Average tumor weight of control mice}} \right) \times 100$.

TABLE 2

Antitumor activity of subcutaneously administered LC 9018

| Dose (mg/kg) | Inhibition rate* |
|---|---|
| 0 (Control) | 0 |
| 4 | 39.3 |
| 40 | 84.4 |

Sarcoma 180 (1-2 × 10⁶ cells/mouse) was inoculated subcutaneously into ICR mice. LC 9018, suspended in saline, was injected subcutaneously 24 hr after the tumor inoculation. Animals were dissected 3 weeks after the inoculation and the weight of the tumor was measured.

*Inhibition rate was calculated as for Table 1.

TABLE 3

Antitumor activity of orally administered LC 9018

| Total dose (mg/kg) | Inhibition rate* |
|---|---|
| 0 (Control) | 0 |
| 1200 | 70.5 |
| 2000 | 64.2 |

Sarcoma 180 (1-2 × 10⁶ cells/mouse) was inoculated subcutaneously into ICR mice on day 0. LC 9018 was given orally daily on days −10, +1, and +10. Animals were dissected 3 weeks after the inoculation of tumor cells and the weight of the tumor was measured.

*Inhibition rate was calculated as for Table 1.

TABLE 4

Antitumor activity of intraperitoneally administered LC 9018 against intraperitoneally inoculated Sarcoma 180

| Total dose (mg/kg) | T/C %* |
|---|---|
| 0 (Control) | 100 |
| 1 | 104 |
| 10 | 367 |
| 40 | 243 |

Sarcoma 180 (1-2 × 10⁶ cells/mouse) was inoculated intraperitoneally on day 0. LC 9018, suspended in saline, was injected intraperitoneally daily on days −5−−1.

$$*T/C \% = \frac{\text{Average survival time of tested mice}}{\text{Average survival time of control mice}} \times 100.$$

TABLE 5

Antitumor activity of LC 9018 against mouse leukemia

| Leukemia cell | Total dose (mg/kg) | T/C %* |
|---|---|---|
| L1210 | 0 (Control) | 100 |
| | 6 | 119 |
| | 12 | 128** |
| | 60 | 138*** |
| | 120 | 127** |
| P-388 | 0 (Control) | 100 |
| | 5 | 120** |
| | 50 | 118** |
| | 250 | 108 |

Mouse leukemia L1210 or P-388 (1 × 10⁵ cells/mouse) was inoculated intraperitoneally into BDF₁ mice on day 0. LC 9018, suspended in saline, was given intraperitoneally daily on days +1−+5.
*T/C % was calculated as for Table 4.
**P < 0.005.
***P < 0.0001.

TABLE 6

Acute toxicity of lactobacilli and streptococcal preparation

| Route | Strain or preparation | LD₅₀(mg/kg) male | female |
|---|---|---|---|
| i.p. | L. casei YIT 9018 (LC 9018) | 650 | 730 |
| | L. casei N VIII - 1 | 515 | 581 |
| | L. casei TK IV - 2 | 350 | 466 |
| | L. acidophilus YIT 0163 | 550 | 612 |
| | L. salivarius YIT 0104 | 504 | 566 |
| | L. plantarum YIT 0158 | 340 | 361 |
| | L. bulgaricus YIT 0046 | 310 | 358 |
| | L. delbrueckii YIT 0080 | 256 | 283 |
| | Streptococcal preparation | 125 | 140 |
| i.v. | L. casei YIT 9018 (LC 9018) | 156 | 240 |
| | Streptococcal preparation | 24.5 | 25.5 |
| s.c. | L. casei YIT 9018 (LC 9018) | 2500 | 2500 |
| | Streptococcal preparation | 238 | 197 |
| p.o. | L. casei YIT 9018 (LC 9018) | 5000 | 5000 |
| | Streptococcal preparation | 500 | 500 |

Lactobacilli or streptococcal preparation was given to ICR mice (body weight of about 25 g) intraperitoneally (i.p.), intravenously (i.v.), subcutaneously (s.c.) or orally (p.o.).

What we claim is:

1. A composition for inhibiting tumor growth, which comprises a tumor growth-inhibiting amount of whole cells of *Lactobacillus casei* YIT 9018 and a physiologically acceptable saline carrier.

2. A composition according to claim 1, wherein the *Lactobacillus casei* YIT 9018 is heat-killed *Lactobacillus casei* YIT 9018 whole cells.

3. A composition for inhibiting tumor growth, which comprises a tumor growth-inhibiting amount of whole cells of *Lactobacillus casei* YIT 9018 and hydroxypropyl cellulose.

4. A composition according to claim 3, wherein the *Lactobacillus casei* YIT 9018 is heat-killed *Lactobacillus casei* YIT 9018 whole cells.

5. A method of inhibiting tumor growth in an animal, which comprises administering to the animal a tumor growth-inhibiting amount of whole cells of *Lactobacillus casei* YIT 9018.

6. A method according to claim 5, wherein the *Lactobacillus casei* YIT 9018 is heat-killed *Lactobacillus casei* YIT 9018 whole cells.

7. A method according to claim 5 or 6, wherein the *Lactobacillus casei* YIT 9018 is administered in admixture with a physiologically acceptable saline carrier.

8. A method according to claim 5 or 6, wherein the *Lactobacillus casei* YIT 9018 is administered in admixture with hydroxypropyl cellulose.

* * * * *